US00PP31454P2

(12) United States Plant Patent
Hansen

(10) Patent No.: US PP31,454 P2
(45) Date of Patent: Feb. 18, 2020

(54) ***DIANTHUS* PLANT NAMED 'APPLEBLOSSOM BURST'**

(50) Latin Name: ***Dianthus* hybrid**
Varietal Denomination: Appleblossom Burst

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,942

(22) Filed: Feb. 1, 2019

(51) Int. Cl.
*A01H 5/02* (2018.01)
*A01H 6/30* (2018.01)

(52) U.S. Cl.
USPC ..... Plt./276

(58) Field of Classification Search
USPC ..... Plt./272, 276
See application file for complete search history.

*Primary Examiner* — Susan McCormick Ewoldt

(57) ABSTRACT

A new and unique plant cultivar of perennial carnation or pinks, *Dianthus* plant named 'Appleblossom Burst' with numerous, medium-sized, semi-double, lightly-fragrant flowers producing a rounded slightly mounded face. The numerous, well-branched stems cover top to bottom of clump with multiple flowers per stem. Petals open light pink blushed with medium pink and lighten in maturity to white to white with faint pink blush. Center of flowers has a dark red eye, and petal tips have fine serrations. The habit is compact with narrow, bluish-green foliage.

1 Drawing Sheet

Botanical denomination: *Dianthus* hybrid;
Cultivar designation: 'Appleblossom Burst';

STATEMENT REGARDING PRIOR DISCLOSURES UNDER 37 CFR 1.77(b)(6)

The first public disclosure of the claimed plant, in the form of a website to the public and email release to customers, was made by Walters Gardens, Inc. on Feb. 1, 2018. The first sales of the claimed plant was on Jul. 9, 2018 by Walters Gardens, Inc. Walters Gardens, Inc. obtained the new plant and information about the new plant directly from the inventor. No plants of *Dianthus* 'Appleblossom Burst' have been sold, in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct cultivar of carnation or pinks from the genus *Dianthus* and given the cultivar name 'Appleblossom Burst'. The new plant was the result of an intentional cross on May 14, 2012 under the direction of the inventor between *Dianthus* 'WP05 Yves' U.S. Plant Pat. No. 18,828 as the female or seed parent and 'Sweetie Pie' U.S. Plant Pat. No. 27,989 as the male or pollen parent. The cross was harvested and sown in June of 2012. The new hybrid was first selected from trials at a wholesale perennial nursery in Zeeland, Mich. during the summer of 2014 as a single seedling clone and given the breeder code number 13-34-102 later in the evaluation processes. *Dianthus* 'Appleblossom Burst' has been asexually propagated at the same nursery in Zeeland, Mich. since 2014 using traditional shoot tip cutting and shoot tip tissue culture procedures and found to reproduce plants that are identical and exhibit all the characteristics of the original plant.

SUMMARY OF THE INVENTION

*Dianthus* 'Appleblossom Burst' has not been evaluated under all possible environmental conditions. The phenotype may vary with variations in environment including: growing temperature, available sunlight, nutrients, water, etc. without a change in the genotype of the plant.

Compared with the new plant, the female parent 'YP05 Yves' is taller in habit, has flowers that are white with bright plum center, fifteen to twenty petals per flower and three to seven inflorescences per stem. 'Sweetie Pie' has flowers that are true pink with a subtly dark pink eye and the flower colors do not change as significantly. The nearest comparison cultivars known to the inventor are: 'Pomegranate Kiss' U.S. Plant Pat. No. 21,895, 'Electric Red' U.S. Plant Pat. No. 29,591, 'Devon Flavia' U.S. Plant Pat. No. 15,903, 'Stardust' U.S. Plant Pat. No. 20,999 and copending application Ser. No. 16/350,940, 'Cute as a Button'. The flower petals of 'Coral Reef' are primarily a lighter reddish coral color with fewer petals than the new plant. 'Pomegranate Kiss' has a deep red petals in the center with lighter margins of rose pink. 'Devon Flavia' has more uniform pink flowers without the dark reddish bar. 'Stardust' has flowers that are coral pink in color and do not have the dark reddish purple bar. 'Cute as a Button' has flowers of medium pink with large deep red eye, the petal colors do not change as significantly and the habit is slightly larger.

*Dianthus* 'Appleblossom Burst' is distinct from its parents and all other *Dianthus* known to the applicant in the following combined traits:

1. Semi-double flowers opening up with a full slightly rounded face.

2. Petals open a light pink blushed with medium pink and mature to white to near white with darker red bar near the base of the petal limb.
3. Petal margin is finely toothed;
4. Multiple flowers per stiff, upright peduncle;
5. Medium flower size producing a lightly-sweet spicy fragrance;
6. Compact habit and dense blue-green foliage.

BRIEF DESCRIPTION OF THE DRAWINGS

The photographs of 'Appleblossom Burst' are of a two-year-old plant grown in full-sun trial garden in Zeeland, Mich. showing the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
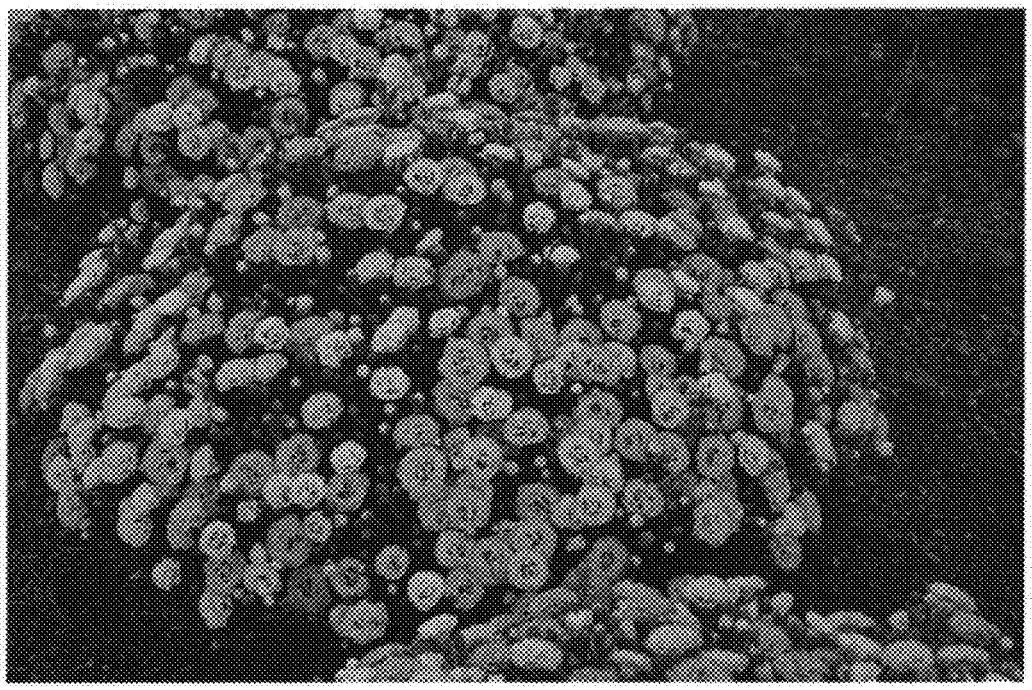
FIG. 1 shows the habit of the plant in mid-season flowering.
Figure 2:
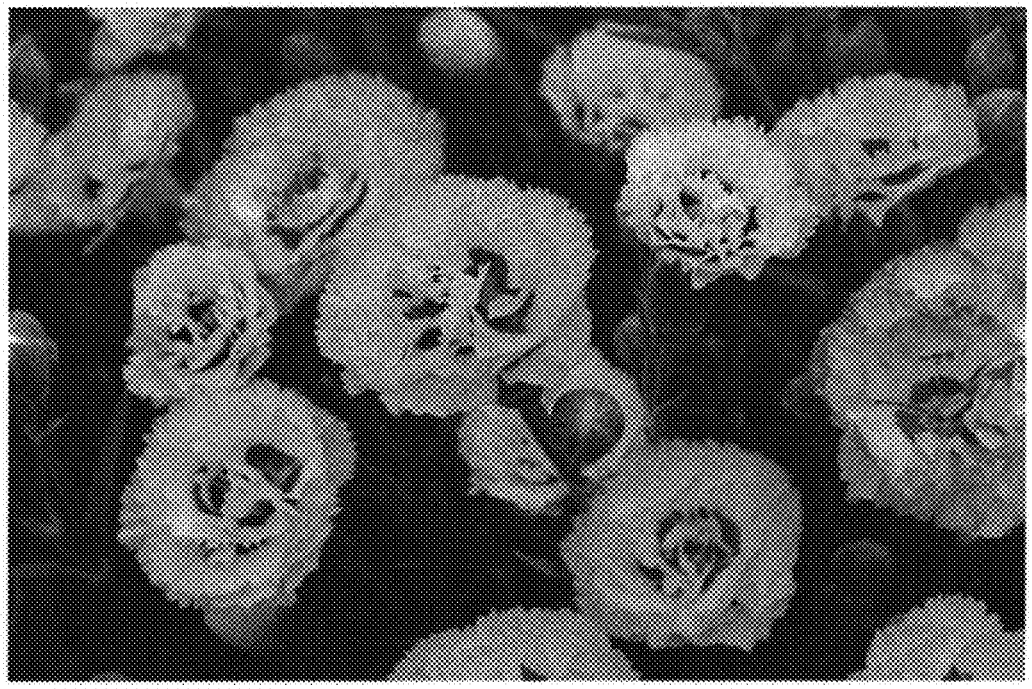
FIG. 2 shows a close-up of the flowers and bud.

The following detailed description of 'Appleblossom Burst' is based on observations of two-year-old plants grown in a full-sun trial garden and also in a partially shaded greenhouse at a nursery in Zeeland, Mich. with supplemental watering, light additions of fertilizer. All color usage is in accordance with the 2015 edition of The Royal Horticultural Colour Chart except where common dictionary terms are used.

Botanical classification: *Dianthus* hybrid;

Parentage: *Dianthus* 'WP05 Yves' as the female or seed parent, and 'Sweetie Pie' as the male or pollen parent;

Plant habit: Caespitose, herbaceous, evergreen, winter-hardy perennial; stems and peduncles highly branched, mostly erect stems; height of foliage about 18.0 cm and about 44.0 cm across; height in flower is about 25.0 cm; Root system; fine, fibrous; color nearest RHS 155D;

*Vigor*.—Good, spring planted plugs finish in 3.8 liter pots in seven to eight weeks.

Foliage:

*Leaf type*.—Simple, linear, opposite, decussate, sessile, glabrous, glaucous both adaxial and abaxial; margin entire to microscopically serrulate; acute narrowly apex; base truncate, decurrent, clasping; no fragrance detected.

*Leaf dimensions*.—To about 8.5 cm long and about 4.0 mm wide, average about 7.3 cm long and 3.5 mm wide.

*Leaf color*.—Young expanding leaves adaxial and abaxial between RHS 144A and RHS 143C; mature abaxial nearest RHS N138A and adaxial blend between RHS N138A and RHS 189B.

*Venation*.—Not pronounced; obscurely pinnate, coloration same as that of leaf top and bottom.

Stems: About 40 per plant; upright; cylindrical, glabrous, glaucous; solid; branching in upper nodes;

*Stem size*.—About 12.5 cm long to peduncle and about 3.0 mm wide at base.

*Stem color*.—Blend between RHS 145D and RHS 142D.

*Branching*.—Numerous; typically alternate from upper nodes; about 10 per main stem and about 300 per plant; branch size average about 3.5 cm long and 1.5 mm diameter at time of initial flowering.

*Nodes*.—About 3.0 mm across; color nearest RHS 142D.

*Internodes*.—About 21 per stem before peduncle; average about 6.5 mm apart depending on growing temperature, shorter in cooler conditions.

Inflorescence:

*Type*.—Terminal, cymose; salverform; actinomophic; semi-double.

*Attitude*.—Upright to slightly outward around perimeter of plant.

*Dimension*.—About 3.0 cm across and extending about 3.8 cm above base of calyx tube and 7.0 mm wide at apex of calyx.

*Flowers per stem*.—3 to 5, average 3.5.

*Pedicel*.—Glaucous, glabrous, cylindrical, stiff; primarily upright.

*Pedicel size*.—Terminal flower to about 6.5 mm long and about 2.0 mm diameter; other flowers average about 3.0 mm long and 1.5 mm diameter.

*Pedicel color*.—Nearest blend between RHS N138D and RHS 189B.

*Flower bud*.—Slowly opening; glabrous; glaucous; with calyx still closed: ellipsoid with rounded base and acute apex; about 20.0 mm long and 8.0 mm across at distal fusion point of sepals; with petals extended beyond calyx and still parallel to calyx side: cylindrical, with rounded base and truncate apex or petal tops, about 24.0 mm long and 8.0 mm across near apices of petals.

*Flower bud color*.—With petals enclosed in calyx nearest RHS 146C in basal portion and distally nearest RHS N138B; with petals extended beyond calyx petal portion nearest RHS N155B.

*Flower period*.—Beginning late spring and continuing for about three weeks.

*Flower fragrance*.—Light, sweet spicy, clove-like.

*Flower lasting quality*.—Individually about seven to ten days on or cut from plant.

*Petals*.—Glabrous; 12 to 24 per flower; consisting of a rounded blade or limb and a claw; limb and claw combined are flabellate; limb apex and margin with fine irregular dentations average 1.0 mm wide and 1.0 mm long; limb bent outwardly in distal 16.0 mm to nearly a ninety degree angle creating a slightly rounded face; persistent.

*Petal dimensions*.—Limb to about 20.0 mm across, average about 17.0 mm across; claw tapering to attenuate base of about 1.0 mm across; whole petal to about 32.0 mm long, average about 29.0 mm long.

*Petal color*.—Young abaxial claw nearest RHS 145D, young abaxial limb lighter than RHS N155B; young adaxial claw nearest RHS 145D, young adaxial limb nearest RHS 63C with 3.0 mm long bar stretching from base of limb between RHS 71A and RHS 61A; mature abaxial claw nearest RHS 145D, mature abaxial limb nearest RHS N155B; mature adaxial claw nearest RHS 145D, mature adaxial limb nearest RHS N155B to nearest RHS NN155D with faint blush of nearest RHS N155B with said bar nearest RHS.

*Calyx*.—Terete to campanulate; to about 18.0 mm long and 7.0 mm diameter at apex.

*Sepals*.—Five; acute apex and fused in basal 15.0 mm forming five-toothed calyx tube; glabrous; glaucous abaxial; margins entire to micro-ciliolate.

*Sepal size*.—Individually about 18.0 mm long and about 4.0 mm across at distal fusion.

*Sepal color*.—Abaxial margin translucent to nearest RHS 157D, mid-portion nearest RHS 137B with heavy glaucous covering nearest RHS 189C, base nearest RHS 146D; adaxial margin translucent to nearest RHS 157D, mid-portion nearest RHS 147C, base nearest RHS 147D.

*Peduncle*.—Glabrous; glaucous; solid, cylindrical; stiff; about 8.0 cm long and about 2.5 mm diameter at base; attitude mostly upright.

*Peduncle color*.—Blend between RHS N138C and RHS 189B with light glaucous bloom, nearest RHS 138A without glaucous bloom.

*Epicalyx*.—Two pairs subtending each flower; opposite, glaucous, glabrous; sessile, margin entire, broadly cordate; inner pair with broadly acute apex and truncate base; outer pair with acuminate apex truncate base; and outer pair about 6.0 mm long and about 4.5 mm wide; inner pair about 7.5 mm long and about 8.5 mm across near middle.

*Epicalyx color*.—Both pairs abaxial variably apex nearest RHS 137A, margin translucent to nearest RHS 155C and middle portion nearest RHS 137A and perimeter nearest RHS 160C; adaxial apex nearest RHS 137A, center and base nearest RHS 137D, margin translucent to nearest RHS 160D.

Androecium: Not observed;

Gynoecium: Single; to about 17.0 mm long;

*Style*.—Bifurcate just above ovary; puberulent; to 12.0 mm long; color nearest RHS N75C.

*Stigma*.—Slightly flattened abaxial to adaxial; about 5.0 mm long and 1.0 mm wide; color nearest RHS N155D blushed with RHS N75D in adaxial surface.

*Ovary*.—Superior; ellipsoid-shaped with broadly acute apex and truncate base; about 5.0 mm long and 5.5 mm wide; color between RHS 150D and RHS 145D.

Fruit and seed: Not observed;

Disease resistance: The new plant is resistance to center die out from fungus or high temperatures. The plant grows best with adequate moisture and well-drained soil, but is able to tolerate some drought once established. Hardiness at least from USDA zone 4 through zone 9.

It is claimed:

1. A new and distinct *Dianthus* plant named 'Appleblossom Burst' essentially as herein described and illustrated.

* * * * *